United States Patent [19]

Levitov

[11] Patent Number: 5,383,857
[45] Date of Patent: Jan. 24, 1995

[54] SAFETY SYRINGE

[75] Inventor: Alexander B. Levitov, Maplewood, Minn.

[73] Assignee: Abbis Corporation, St. Paul, Minn.

[21] Appl. No.: 223,159

[22] Filed: Apr. 5, 1994

[51] Int. Cl.6 .............................................. A61M 5/00
[52] U.S. Cl. .................................... 604/110; 604/198
[58] Field of Search ............... 604/110, 198, 263, 187

[56] References Cited

U.S. PATENT DOCUMENTS

| | | | |
|---|---|---|---|
| 4,923,447 | 5/1990 | Morgan | 604/198 |
| 4,927,416 | 5/1990 | Tomkiel | 604/198 |
| 5,002,533 | 3/1991 | Julien | 604/110 |
| 5,098,401 | 3/1992 | DeLange | 604/192 |
| 5,147,303 | 9/1992 | Martin | 604/110 |
| 5,188,600 | 2/1993 | Julien | 604/110 |
| 5,242,420 | 9/1993 | Martin | 604/198 |
| 5,269,761 | 12/1991 | Stehrenberger et al. | 604/110 |

*Primary Examiner*—John D. Yasko
*Attorney, Agent, or Firm*—Merchant, Gould, Smith, Edell, Welter & Schmidt

[57] ABSTRACT

A moveable guard sheath is released and moved over the length of the syringe barrel to prevent contact which the syringe needle.

4 Claims, 7 Drawing Sheets

SAFETY SYRINGE

FIELD OF THE INVENTION

The present invention relates to a medical syringe and more particularly to a syringe and guard sheath assembly.

BACKGROUND ART

Presently available disposable syringes do not adequately safe guard the user from unintentional contact with the needle of the syringe. Many guard structures have been proposed but they suffer from several drawbacks. In many instances the user must manually retract the needle into a guard structure or otherwise cap the needle structure. These approaches force the user to move his hand toward the needle and therefore expose the user to a greater risk of accidental prick by a contaminated needle. Consequently there is a need for an improved safety syringe which minimizes this risk.

SUMMARY

The present invention addresses this problem and provides a safety syringe which automatically covers the needle after the contents of the syringe has been dispensed into the patient.

Structurally the safety syringe assembly 10 includes a syringe plunger 12 and syringe barrel 14. Together these two elements are used to form a reservoir for the medicament. A guard sheath 16 fits over the syringe barrel 14 and may slide in a set of tracks. This guard sheath 16 may move from a retracted position to an extended position. In normal use, the safety syringe assembly 10 is dispensed with the guard sheath 16 in the extended position. The user may move the guard sheath 16 into the retracted position against a restoring force supplied by an elastomeric spring 18. The guard sheath 16 is retained in the retracted position by a latch mechanism. In this retracted position the user may attach a needle 20 to the syringe barrel 14. The user may next fill the syringe by withdrawing the syringe plunger 12 from the syringe barrel 14. Next the operator inserts the needle 20 into the patient to make the injection. At the end of the operating stroke of the syringe plunger 12 the user withdraws the needle from the patient. Next slight additional motion is imparted to the plunger and a latch release surface 28 located on the syringe plunger 12 intercepts a pair of latch arms to release the guard sheath 16. Once released the guard sheath moves toward the extended position covering the needle 20.

The automatic release of the guard sheath 16 efficaciously covers the needle without further manipulation by the user. One handed operation consistent with normal syringe use is preserved.

BRIEF DESCRIPTION OF THE DRAWINGS

An illustrative and exemplary form of the invention is shown in the drawings. Identical reference numerals identify identical structure throughout the several views wherein.

DETAILED DESCRIPTION

Figure 1:
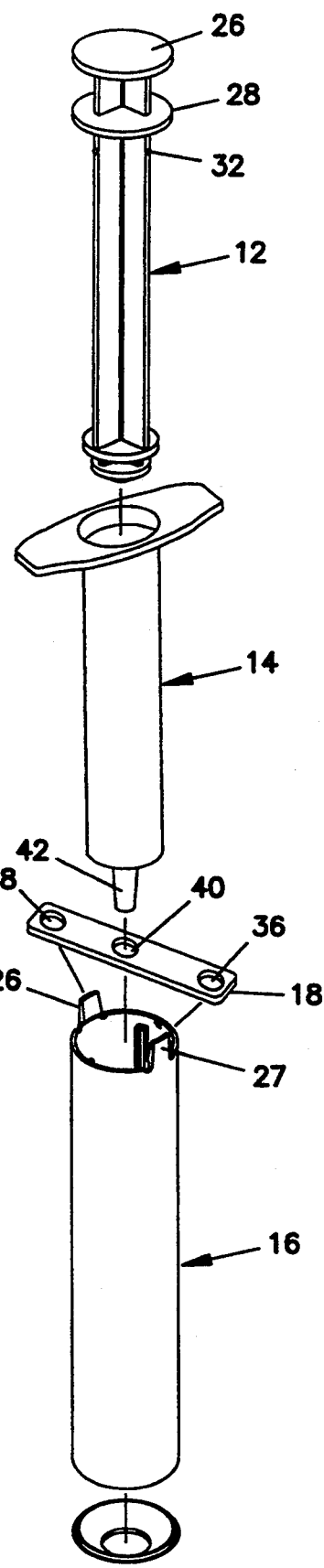
FIG. 1 is an exploded view of the safety syringe.

FIG. 1 shows the safety syringe 10 assembly in an exploded view. The syringe plunger 12 is fitted inside the bore of the syringe barrel 14. The syringe plunger 12 has a thumb rest 26 which may be grasped by the user. Near the thumb rest 26 is a latch release surface 28.

The syringe barrel 14 includes a finger rest or flange 30 and needle mounting nose 42.

An elastomeric spring 18 is provided with three attachment apertures. The first attachment aperture 36 fits over a latch arm 27 and the second aperture 38 fits over latch arm 26 which are preferably formed integrally with the guard sheath 16. The central aperture 40 receives the nose 42 of the syringe barrel 14. The elastomeric spring 18 when stretched, provides a force between the guard sheath 16 and the syringe barrel 14.

Figure 2:
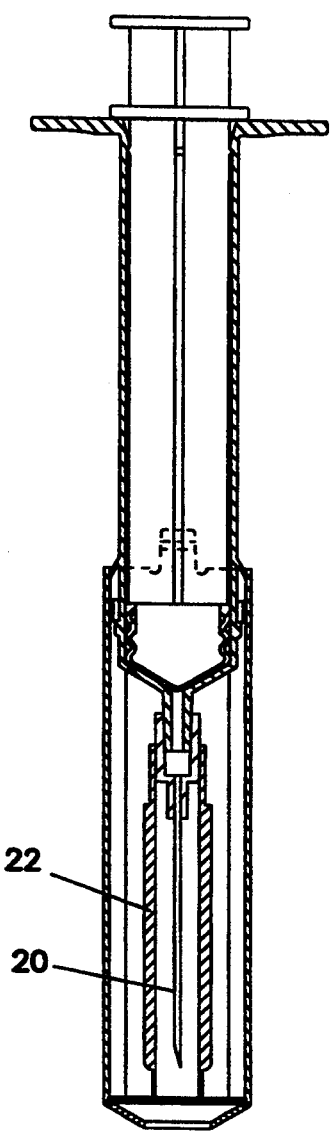
FIG. 2 is a cross section view of the safety syringe.

FIG. 2 is a cross section view of several components assembled and configured for dispensing the safety syringe. In this view the elastomeric spring 18 is excluded to simplify the view. In this view the guard sheath 16 is in the extended position which represents the preferred configuration for dispensing the product. In this extended position the elastomeric spring 18 is in the relaxed state and the syringe plunger 12 is advanced to the end of the bore of the syringe barrel 14. In general the product will be dispensed without a needle attached to the syringe barrel and with the syringe plunger advanced to the limit of its travel. Although in this view a needle 20 and protective cover 22 are shown coupled to the nose 42 of the syringe barrel 14.

Figure 3:
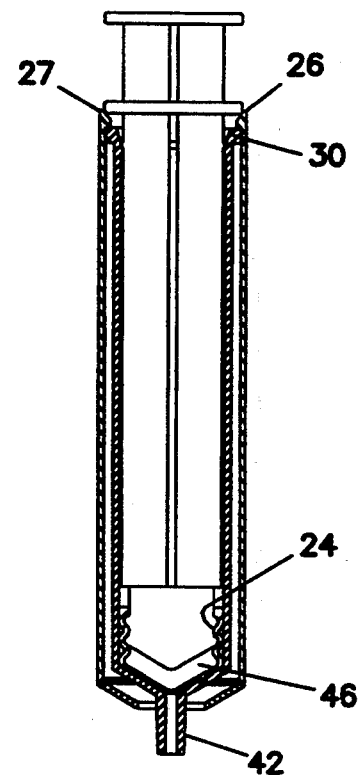
FIG. 3 is a cross section view of the safety syringe.

FIG. 3 shows the safety syringe 10 with the sheath 16 in the retracted state. In general, the user will push the guard sheath 16 into this retracted position where latch arm 26 and latch arm 27 couple with the flange 30. If the plunger 12 is advanced further into the barrel from the position shown in FIG. 3 then the clearance volume 46 will be reduced and the latch arms released from the flange 30.

It is important to note that the guard sheath 16 remains in the latched state depicted in FIG. 3 throughout the filling of the reservoir and throughout the dispensing of the medicament. Only at the conclusion of the injection is the latch released allowing the guard sheath 16 to cover the needle 20. Although the syringe plunger may be equipped with a gasket of conventional design it is preferred to use a gasket 24 which incorporates a small clearance volume seen throughout the figures and identified in FIG. 3 as clearance volume 46. The clearance volume 46 permits the syringe plunger 12 to move distally after the reservoir is emptied. This additional motion is provided to ensure a reliable release of the latch arms by release surface 28. The clearance volume 46 also ensures that the reservoir is emptied prior to release of the latched guard sheath 16. Additional tactile feedback may be supplied to the user by dimples typified by dimple 32. These dimples are located on the plunger 12 and are most easily seen in FIG. 1. In use these dimples contact the interior of the syringe barrel 14 bore as the gasket 24 covers the central lumen of the nose 42. The user forces the dimples into the bore during latch release, which provides a tactile confirmation that the latch release has occurred.

Figure 4:
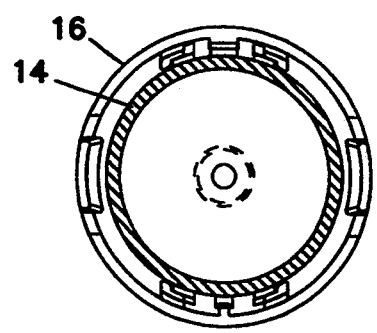
FIG. 4 is a cross section view of the safety syringe.
Figure 5:
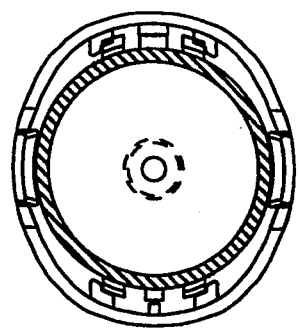
FIG. 5 is a cross section view of the safety syringe.

FIG. 4 and FIG. 5 should be considered together. In FIG. 5 the sheath 16 is in a relaxed state and has a substantially circular outer diameter. In this position mechanical stops formed on the interior of the guard sheath 16 and on the exterior of the syringe barrel 14 are interlocked to retain the guard sheath in the extended position depicted in FIG. 2. To move the guard sheath into the retracted position depicted in FIG. 3 it is necessary to release these interlocks which is accomplished by squeezing the guard sheath 16 as seen in FIG. 5. In this position the stop elements are moved out of abutment and the sheath is free to move.

Figure 6:
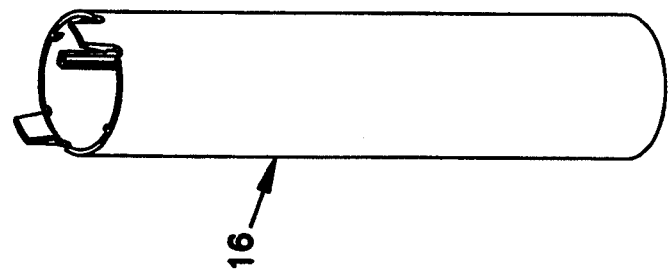
FIG. 6 is an isometric view of a portion of the safety syringe.

FIG. 6 is a perspective view of the guard sheath 16. A set of guide rails is formed on the interior surface of the guard sheath 16 serve to guide the guard sheath 16 during motion from the retracted position to the extended position.

Figure 7:
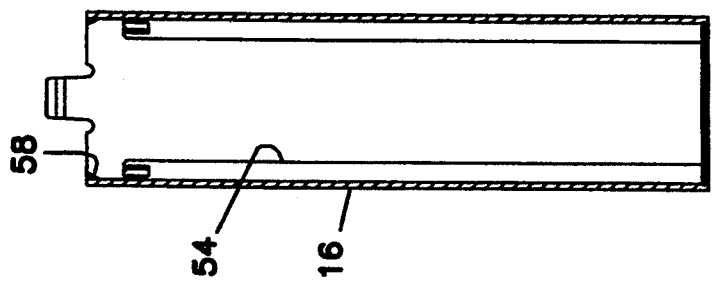
FIG. 7 is a cross section view of a portion of the safety syringe.

FIG. 7 is sectioned along plane A—A and shows that the guide rail 54 extends into the interstitial area between the syringe barrel 14 and the guard sheath 16.

Figure 8:
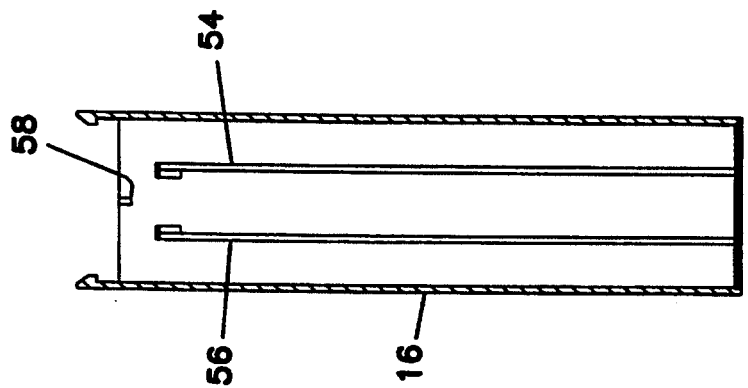
FIG. 8 is a cross section view of a portion of the safety syringe.

FIG. 8 is sectioned along plane B—B and shows that rail 54 is parallel to rail 56. This view also shows the sheath retention nub 58 in isolation. This small ramp like protuberance extends into the area between the sheath and the barrel. In operation the rapid motion of the sheath under the force of the elastomeric spring cause this nub 58 to overrun a companion barrel retention nub 60 to lock the sheath and barrel together in the extended position.

Figure 10:
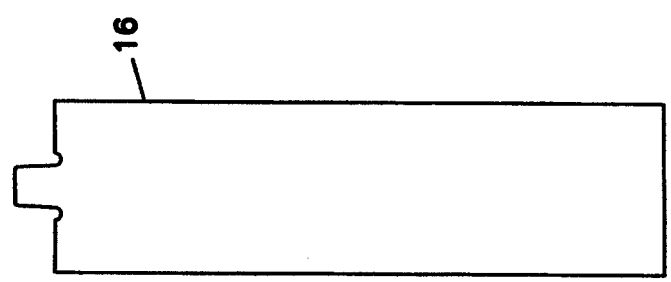
FIG. 10 is a side view of a portion of the safety syringe.
Figure 9:
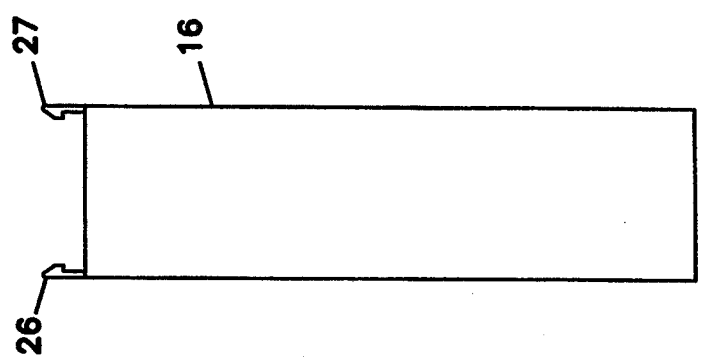
FIG. 9 is a side view of a portion of the safety syringe.

FIG. 9 and FIG. 10 shows the exterior surfaces of the guard sheath 16 and illustrates a preferred but not limiting shape for the latch arm 26 and latch arm 27. In general, it is preferred to have a hooked portion at the end of each latch arm to overly the flange 30 in the retracted position. This shape is preferred because the companion release surface 28 on the plunger 12 is readily adapted to move the hook elements off the flange 30 to release the guard sheath 16.

Figure 11:
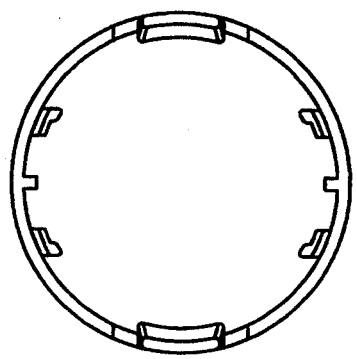
FIG. 11 is a cross section view of a portion of the safety syringe.

FIG. 11 also shows the sheath retention nub 54 located between the guide rail 54 and guide rail 56.

Figure 12:
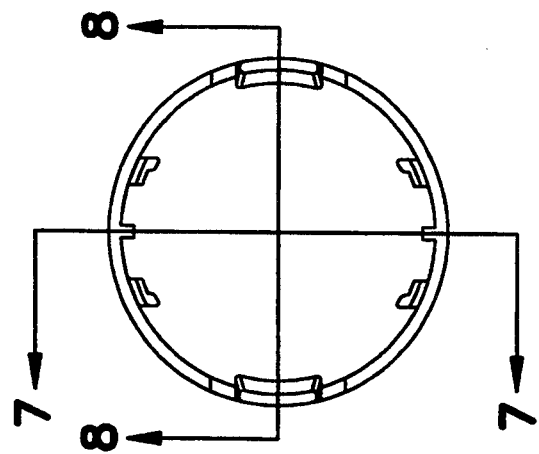
FIG. 12 is a cross section view of a portion of the safety syringe.

FIG. 12 shows the orientation of plane for the companion figures on the sheet of drawings.

Figure 13:
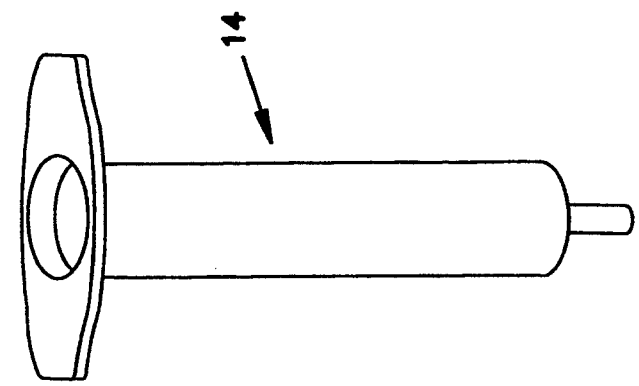
FIG. 13 is an isometric view of a portion of the safety syringe.

FIG. 13 is a perspective view of the syringe barrel 14.

Figure 14:
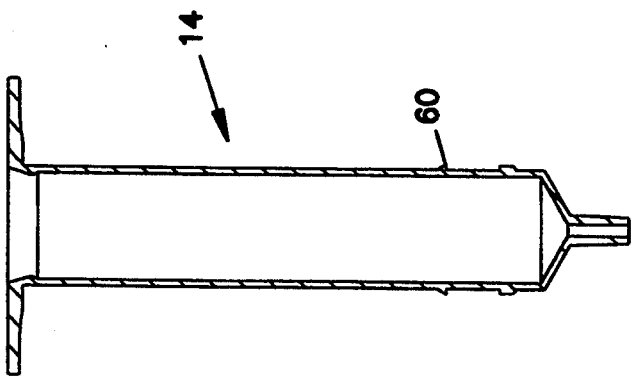
FIG. 14 is a cross section view of a portion of the safety syringe.
Figure 18:
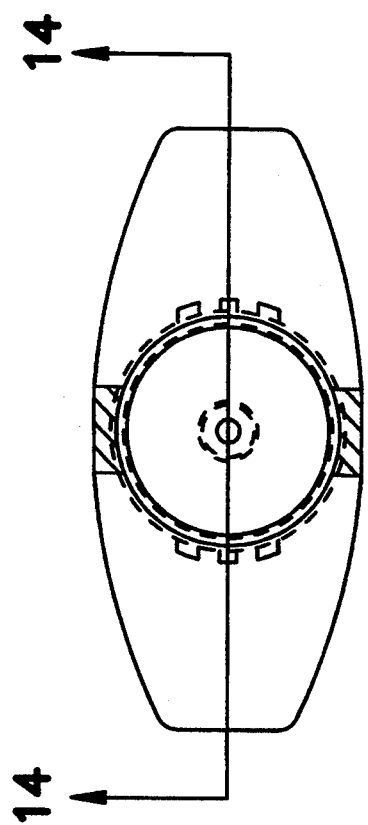
FIG. 18 is a cross section view of a portion of the safety syringe.
Figure 17:
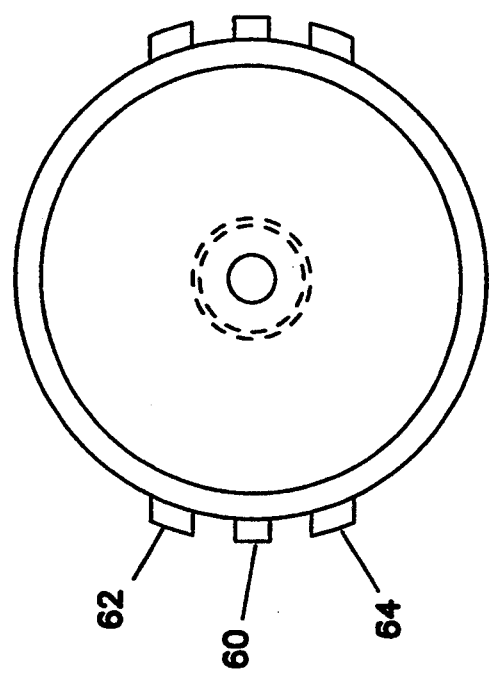
FIG. 17 is a cross section view of a portion of the safety syringe.

FIG. 14 is a cross section taken in the A—A plane ass defined by FIG. 18. In FIG. 14 one of the two preferred retention nubs is shown as nub 60. The height of the nub and the shape of the nub should facilitate mating of the barrel 14 and the sheath 16 in the extended position. As seen in the drawing the presently preferred nub shape is triangular in cross section.

Figure 15:
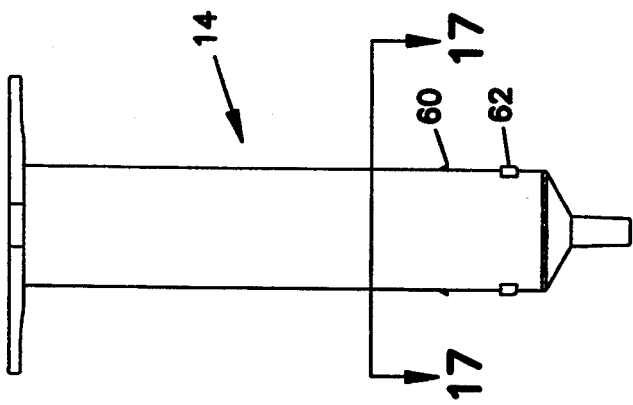
FIG. 15 is a side view of a portion of the safety syringe.

FIG. 15 depicts the positioning of the nub 60 on the exterior surface of the barrel 14 between the two guide block 62 and guide block 64. In this position the nubs do not interfere with the guide rails.

Figure 16:
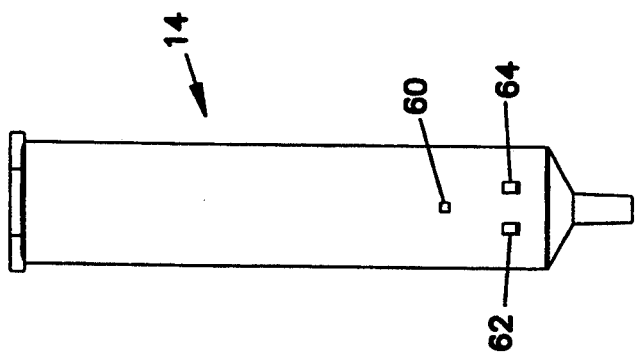
FIG. 16 is a side view of a portion of the safety syringe.

FIG. 16 shows the exterior surface of the barrel 14 rotated to show the relative orientation of the guide block 62 and guide block 64.

Figure 19:
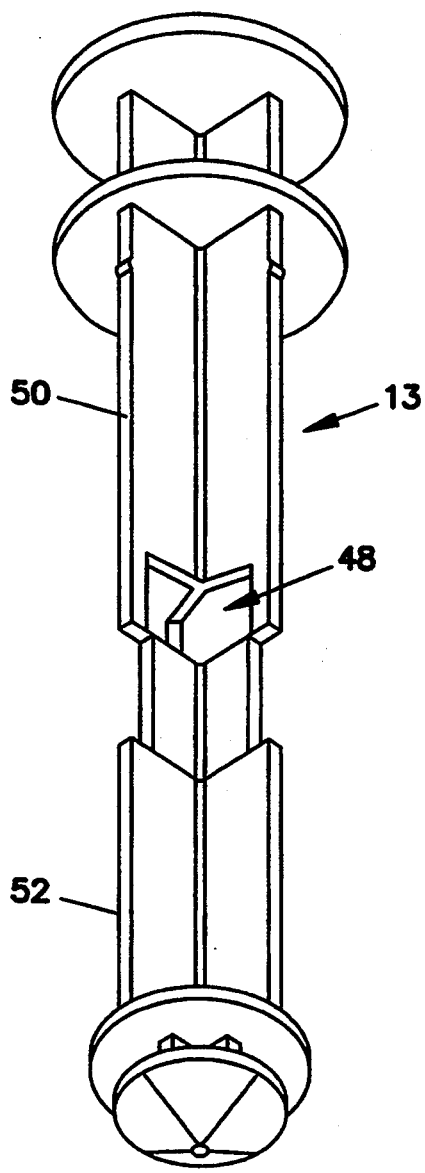
FIG. 19 is an isometric view of a portion of the safety syringe; and,
FIG. 20 is an isometric view of a portion of the safety syringe.
Figure 20:
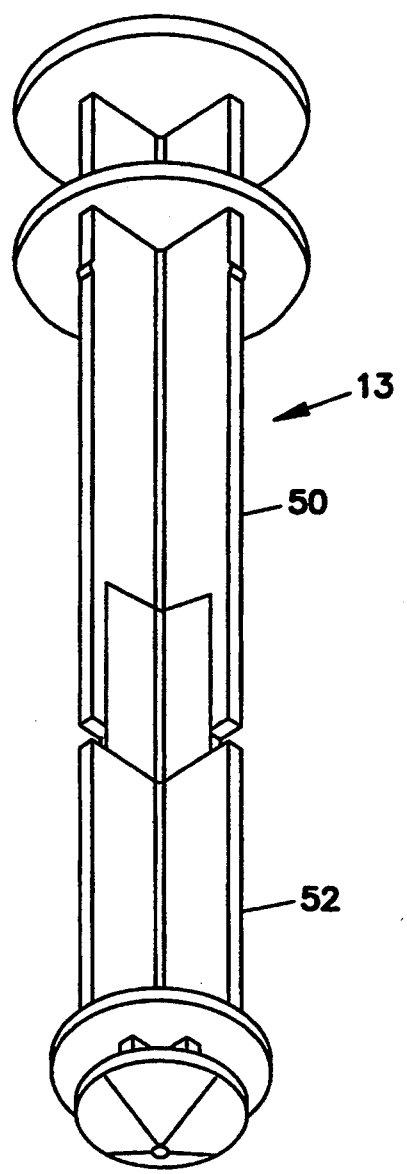

FIG. 19 and FIG. 20 should be considered together and they represent an alternate embodiment of the syringe plunger 12 which prevent reuse of the syringe.

FIG. 19 shows a frangible syringe plunger including a proximal portion 50 and a distal portion 52 which mate at a location 48. As manufactured the two pieces are molded as a unitary structure connected by a fragile web. In use, the web has sufficient strength to permit the reservoir of the syringe to be filled. During the injection of medicament the distal portion 52 bottoms out in the syringe barrel 14 and force supplied by the user breaks the web. Any effort at reusing the syringe assembly 10 would result in extraction of the proximal portion of the syringe from the bore of the syringe barrel rending the syringe inoperable.

What is claimed is:

1. A safety syringe comprising:
   a syringe barrel 14 having a central bore and a nose 42, said nose 42 adapted to receive a needle 20, said syringe barrel having a latch flange 30;
   a guard sheath 16 located for reciprocating motion along said syringe barrel 14 from a first retracted position to a second extended position, said guard sheath 16 having at least one latch arm 26 to couple said guard sheath 16 to said syringe barrel 14 and to retain said guard sheath 16 in said retracted position;
   a syringe plunger 12 having a proximal and distal end, a plunger gasket 24 located on said distal end, and having a thumb rest 26 on said proximal end, said syringe plunger having a latch release surface located proximate said thumb rest 26 for releasing guard sheath 16 as said syringe plunger 12 approaches said latch flange 30;
   an elastomeric spring 18 connected to both said guard sheath 16 and to said syringe barrel 14, and having a relaxed state corresponding to said extended state and having a deflected position corresponding to said retracted position.

2. The safety syringe of claim 1 wherein said gasket 24 includes a clearance volume 46 formed between said gasket and said plunger 12.

3. The safety syringe of claim 1 wherein said syringe plunger 13 includes a frangible web which partitions said syringe plunger upon the application of force, whereby said syringe is disabled after a single use.

4. The safety syringe of claim 1 wherein said elastomeric spring is formed as a apertured web of synthetic rubber.

* * * * *

UNITED STATES PATENT AND TRADEMARK OFFICE
CERTIFICATE OF CORRECTION

PATENT NO. : 5,383,857

DATED : January 24, 1995

INVENTOR(S) : Alexander B. Levitov

It is certified that error appears in the above-identified patent and that said Letters Patent is hereby corrected as shown below:

On the title page:
In [57] ABSTRACT, line 3, before "the syringe needle." please delete the word "which", and insert therefor --with--

In column 4, line 2, please delete the word "ass", and insert therefor --as--

Signed and Sealed this

Twenty-third Day of May, 1995

Attest:

BRUCE LEHMAN

Attesting Officer

Commissioner of Patents and Trademarks